United States Patent [19]
Sanberg et al.

[11] Patent Number: 5,702,700
[45] Date of Patent: Dec. 30, 1997

[54] SERTOLI CELLS AS NEURORECOVERY INDUCING CELLS FOR PARKINSON'S DISEASE

[75] Inventors: Paul R. Sanberg, Spring Hill; Don F. Cameron; Cesario V. Borlongan, both of Lutz, all of Fla.

[73] Assignee: University of South Florida, Tampa, Fla.

[21] Appl. No.: 402,389

[22] Filed: Mar. 13, 1995

[51] Int. Cl.⁶ .................. A01N 63/00; A61K 35/52; A61K 38/22

[52] U.S. Cl. .................. 424/93.1; 424/93.7; 424/562; 424/558

[58] Field of Search .................. 514/2, 44; 435/172.1, 435/172.2, 172.3, 240.1, 320.1; 424/93.2, 93.21

[56] References Cited

U.S. PATENT DOCUMENTS 5,082,670  1/1992  Gage et al. .................. 424/520

FOREIGN PATENT DOCUMENTS

WO9528167  of 1995  WIPO.

OTHER PUBLICATIONS

Carson, et al., *Journal of Biological Chemistry*, Synthesis and Secretion of a Novel Binding Protein for Retinol by a Cell Line Derived from Sertoli Cells, vol. 250 pp. 3117–3123 (1964).

Krieglstein et al EMBO J 14(4):736–742, 1995, Jun. 12, 1997.

Selawry et al., Cell Transplantation, 2:123–129, 1993.

Cameron et al., Transplantation, 50(4):649–653, 1990.

Lindvall et al., Science 247:574–577, 1990.

Bjorklund and Stenevi, "Intracerebral neural grafting: a historical perspective" Bjorklung, A and Steneiv, U. eds, in *Neural Grafting in the Mammalian CNS*, Amsterdam: Elservier, 3–11 (1985).

Bjorklund, "Dopaminergic transplants in experimental Parkinsonism: cellular mechanisms of graft-induced functional recovery" *Current Biology*, 2:683–689 (1992).

Cameron et al., "Successful islet/abdominal testis transplantation does not require Leydig cells" *Transplantation*, 50:649–653 (1990).

Cameron and Muffly, "Hormonal regulation of spermatid binding" *J. Cell Sci.* 100:623–633 (1991).

Griswold, "Protein secretion by sertoli cells: general considerations" in Russell, L.d. and M.D. Griswold eds. *The Sertoli Cell*, Cache River Press, Clearwater, FL, 195–200 (1992).

Isacson et al., "Graft-induced behavioral recovery in an animal model of Huntington's disease" *Proc. Natl. Acad. Sci.*, 83:2728–2732 (1986).

Lindvall et al., "Transplantation in Parkinson's disease: two cases of adrenal medullary grafts to the putamen" *Ann. Neurol.* 22:457–468 (1987).

Lindvall et al., "Grafts of fetal dopamine neurons survive and improve motor function in Parkinson's disease" *Science*, 247:574–577 (1990).

Pakzaban et al., "Increased proportion of Ache-rich zones and improved morphological integration in host striatum of fetal . . . " *Exp. Brain Res.*, 97:13–22 (1993).

Sanberg et al. "Transplantation into central nervous system" in *Cell Transplantation for Huntington's Disease*, R.G. Landes Co., Boca Raton, FL, Chap. 4, pp. 19–21 (1994).

Selawry and Cameron, "Sertoli cell-enriched fractions in successful islet cell transplantation" *Cell Transplan.*, 2:123–129 (1993).

Wictorin et al., "Reformation of long axon pathways in adult rat CNS by human forebrain neuroblasts" *Nature*, 347:556–558 (1990).

Koutouzies et al., "Cell Transplantation for Central Nervous System Disorders" *Critical Reviews in Neurobiology*, 8(3):125–162 (1994).

*Primary Examiner*—Suzanne E. Ziska
*Attorney, Agent, or Firm*—Kohn & Associates

[57] ABSTRACT

A method of generating in situ trophic factor production by transplanting Sertoli cells into the central nervous system of a mammal, the cells creating trophic factors in situ.

1 Claim, 1 Drawing Sheet

SERTOLI CELLS AS NEURORECOVERY INDUCING CELLS FOR PARKINSON'S DISEASE

TECHNICAL FIELD

The present invention generally relates to cell transplantation and specifically to a method of transplanting cells which, following transplantation into the central nervous system (CNS), ameliorates the behavioral deficits associated with neural disorders.

BACKGROUND OF THE INVENTION

Transplantation of neural tissue into the mammalian central nervous system (CNS) has become an alternative treatment for neurodegenerative disorders including epilepsy, stroke, Huntington's diseases, head injury, Parkinson's disease, myelin deficiencies, muscular dystrophy, neurological pain, amyotrophic lateral sclerosis, Alzheimer's disease, and affective disorders of the brain. Preclinical and clinical data indicate that transplanted cells (the graft) used in cell transplantation protocols for these types of neurodegenerative diseases survive and integrate with the host tissue, and provides functional recovery. (Wictorin et al., 1990).

The primary source for these grafts has been the fetus. For example, fetal ventral mesencephalic tissue has been demonstrated to be a viable graft source in Parkinson's disease. (Lindvall et al., 1990; Bjorklund, 1992). Likewise, fetal striatal tissue has been utilized successfully as graft material in Huntington's disease. (Isacson et al., 1986; Sanberg et al., 1994).

Neurologically dysfunctional animals have been transplanted with non-fetal cells. For example, chromaffin cells have been used in the treatment of Parkinson's disease. The major advantage of this type of transplantation protocol is that the graft source is not a fetal source and, thereby, circumvents the ethical and logistical problems associated with acquiring fetal tissue. Utilizing the chromaffin cell protocol, normalization of behavior is observed. However, the functional recovery of this behavior is temporary and the animals revert to their pre-transplantation status. (Bjorklund and Stenevi, 1985; Lindvall et al., 1987). The inability of this type of treatment protocol to maintain normal behavioral activity in animals in the Parkinson's disease model renders clinical application of this protocol as well as other treatment therapies premature.

Long term maintenance of functional recovery has been observed in a diabetic animal model utilizing a novel transplantation treatment protocol utilizing isolated islet cells and Sertoli cells. It is clear that the efficacy of the treatment is due to the presence of the Sertoli cells, in part, due to the Sertoli cell secretory factors. Selawry and Cameron, 1993; Cameron et al., 1990).

Accordingly, it would be desirable to utilize Sertoli cells as a graft source for disease states other than diabetes, specifically, neurodegenerative disorders. The Sertoli cells can be used to function as an in situ factory for trophic factors to thereby ameliorate the behavioral deficits associated with neurodegenerative disorders.

SUMMARY OF THE INVENTION AND ADVANTAGES

In accordance with the present invention, there is provided a method of generating in situ trophic factor production by transplanting Sertoli cells into the central nervous system of a mammal, the cells secreting trophic factors in situ.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
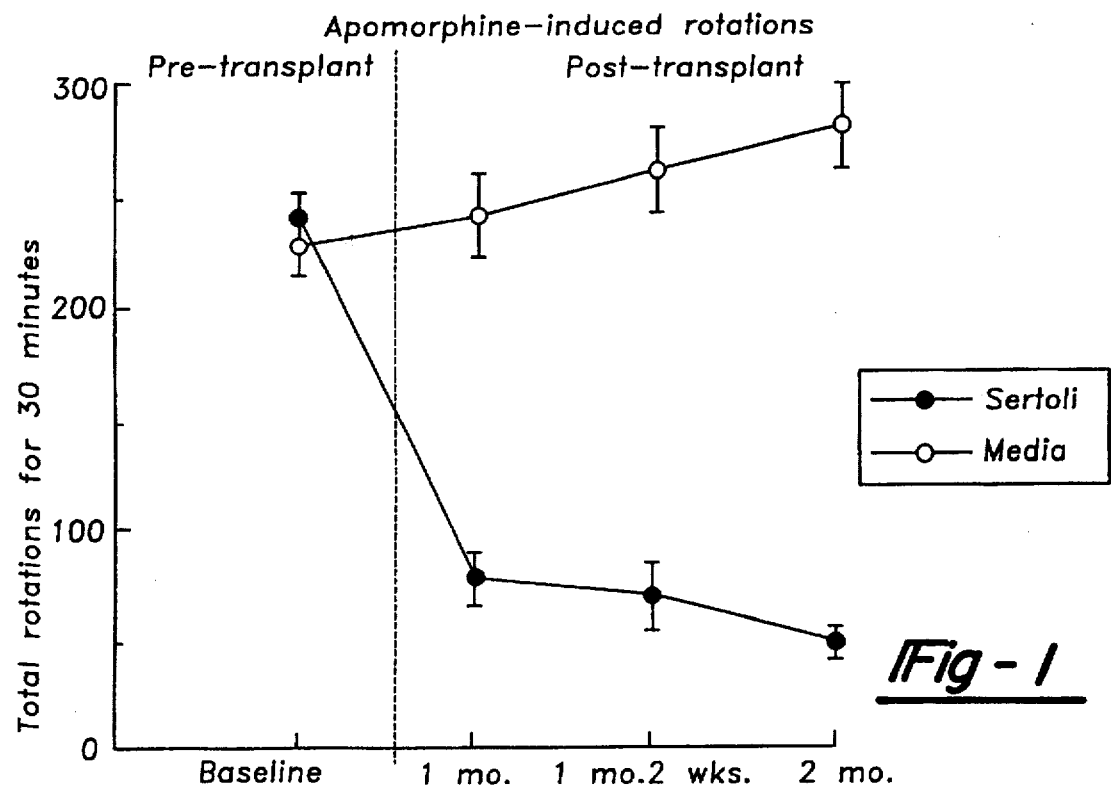
FIG. 1 is a graph showing the results of apomorphine-induced rotational behavior. Animals from both groups exhibited >7 rotations per minute or, at least, a total of 210 rotations for 30 minutes (contralateral to the lesion) when challenged with apomorphine pre-transplant. At post-transplant periods, animals receiving media alone continued to display significant rotations. In contrast, animals receiving the Sertoli cells had a marked reductions (more than 60%) in their rotational behavior across the post-transplant periods.

Generally, the present invention provides a method for promoting the repair and support of dysfunctional nervous tissue by mechanisms including in situ production of Sertoli cell-derived growth and regulatory factors. Additionally, the present method provides a method of generating in situ trophic factor production. This is achieved by transplanting isolated Sertoli cells into the central nervous system of a mammal, the cells secreting trophic factors in situ.

One significant benefit of utilizing Sertoli cells as an in situ factory for producing neurotrophic factors is that Sertoli cells have been shown to have an effective immunosuppressant effect. Accordingly, concomitant adjunctive therapy to produce immunosuppression is not required. In other words, the Sertoli cells can be used as a trophic factor source while also providing a self-induced local immunosuppressive effect.

Trophic factors secreted by Sertoli cells include Sertoli cell-derived growth and regulatory factors such as insulin-like growth factors I and II, epidermal growth factor, transforming growth factors α and β, and interleukin 1α(Griswold, 1992). For a more extensive list of Sertoli cell secretory factors refer to Table 1. Such factors have been shown to have an ameliorative effect on behavioral deficits associated with neurodegenerative diseases. These factors are well know tropic factors which support normal cell and tissue metabolism and function. (Griswold, 1992). The present invention utilized the phenomenon that Sertoli cells can produce a trophic-rich, growth-supportive fluid microenvironment at the site of cellular dysfunction. In contrast to the Sertoli cell/islet cell transplantation protocol used in the diabetic model, the method of the present invention utilizes only one type of cell, i.e. Sertoli cells, thereby significantly reducing the logistic and procedural problems inherent in attempting to transplant two different cell types at one host site.

As demonstrated in the experimental section below, the present invention can be utilized as a treatment for ameliorating the behavioral deficits associated with neurodegenerative diseases, such as Huntington's disease and Parkinson's disease. This can be accomplished without the concomitant side effects of previously utilized immunosuppressive adjuvant therapy, such as the use of cyclosporine A. Additionally, there is less chance of cell separation as where cells are co-transplanted, such as the transplantation of Sertoli cells and chromaffin cells, so that the chromaffin cells would provide growth factors and trophic factors while the Sertoli cells would provide the immunosuppressive effect. Rather, a single type of cell need only be transplanted, the Sertoli cells, to provide both the secretion of the trophic factors and the immunosuppressive effect.

The following example demonstrates the ability of the present invention to ameliorate behavioral deficits associated with neurodegenerative disorders.

Specific Protocol: The protocol generally involves two basic steps, (1) Sertoli cell isolation and (2) cell transplantation both of which are briefly described below (for greater details regarding the cell isolation see Selawry and Cameron (1993) and for details regarding cell transplantation, see reference (Pakzaban et al., 1993).

(1) Sertoli Cell Isolation

The isolation procedure follows a well defined method Selawry and Cameron, (1993) and is routinely utilized. The cell culture medium used in all isolation steps and in which the cells were incubated was DMEM: Hams F12 supplemented with retinol, ITS, and gentamicin sulfate (Cameron and Muffly, 1991). Testes were surgically collected from sixteen day old male Sprague-Dawley rats. The testes were decapsulated and prepared for enzymatic digestion to separate other testicular cell types from the Sertoli cells. The enzymatic procedure utilized collagenase (0.1%), hyaluronidase (0.1%), and trypsin (0.25%) which is a typical procedure used in many cell isolation protocols. After sequential enzymatic digestion, the Sertoli cell isolate was washed with culture medium, transferred to sterile culture vessels and placed in a humidified, 5% $CO_2$–95% air tissue culture incubator. Following forty-eight hours of preincubation in a 39° C. incubator, the Sertoli cells were washed to remove any contaminating debris. The resultant Sertoli cell-enriched fraction was resuspended into 0.25 ml of DMEM/F12 medium and incubated at 37° C. for at least 24 hours.

The Sertoli cells are then liberated from the vessel floor with trypsin, transferred to a sterile conical test tube, and repeatedly washed by centrifugation and treated with trypsin inhibitor to cease the enzymatic action of the trypsin. During the day of transplantation, the Sertoli cell-enriched fraction is resuspended and suctioned using a Hamilton syringe with a 20 gauge spinal needle.

(2) Cell Transplantation

The transplantation protocol follows the procedure as previously described (Pakzaban et al., 1993). Animal surgery was carried out under sterile conditions. All animals were initially anesthetized with 0.60 ml/kg sodium pentobarbital and then were placed in a Koph stereotaxic instrument. Unilateral striatal transplants were performed using coordinates set at V: anteroposterior =+1.2, mediolateral= ±2.8, dorsoventral=6.0, 5.9, and 5.8 (based on the atlas of Paxinos and Watson, 1984). The striatum ipsilateral to the lesioned substantia nigra was transplanted with Sertoli cells. Each striatum receives a total volume of 3 µl of Sertoli cell suspension. One microliter of the Sertoli cell suspension was infused over one minute per dorsoventral site. Another five minutes was allowed upon reaching the last dorsoventral site before retracting the needle. After surgery, the animals were placed on heating pads to recover. Animals receive a short course of immunosuppression using Cyclosporin-A (20 mg/kg/d, i.p.) immediately after surgery and on the day following transplant.

Sertoli cells are transplanted into animal models of various neurodegenerative disorders by stereotaxic coordinates defined for the specific disorder, as illustrated in the Parkinson's disease example, as then are systemically assayed for functional recovery by techniques specific to that animal model.

The present study used Sprague-Dawley male, eight week old rats with 6-OHDA-induced hemiparkinsonism (n=12). At three weeks post-lesion, the animals were subjected to behavioral tests that included the apomorphine-induced rotational behavior and the swing behavior. Baseline data showed significant apomorphine-induced rotational behavior (contralateral to the lesioned side of the CNS) in all these animals (at least 200 turns for 30 minutes). Using the elevated body swing test (EBST), significant right-biased swing activity (more than 70%) was also noted. At three weeks post-lesion, one group of animals (n=6) was subjected to the same surgical procedure but only received media (DMEM without serum). All animals received cyclosporine (20mg/kg) for the first two days following the transplant. At one, one and a half, and two months post-transplant, animals were again introduced in the same behavioral tests.

Figure 2:
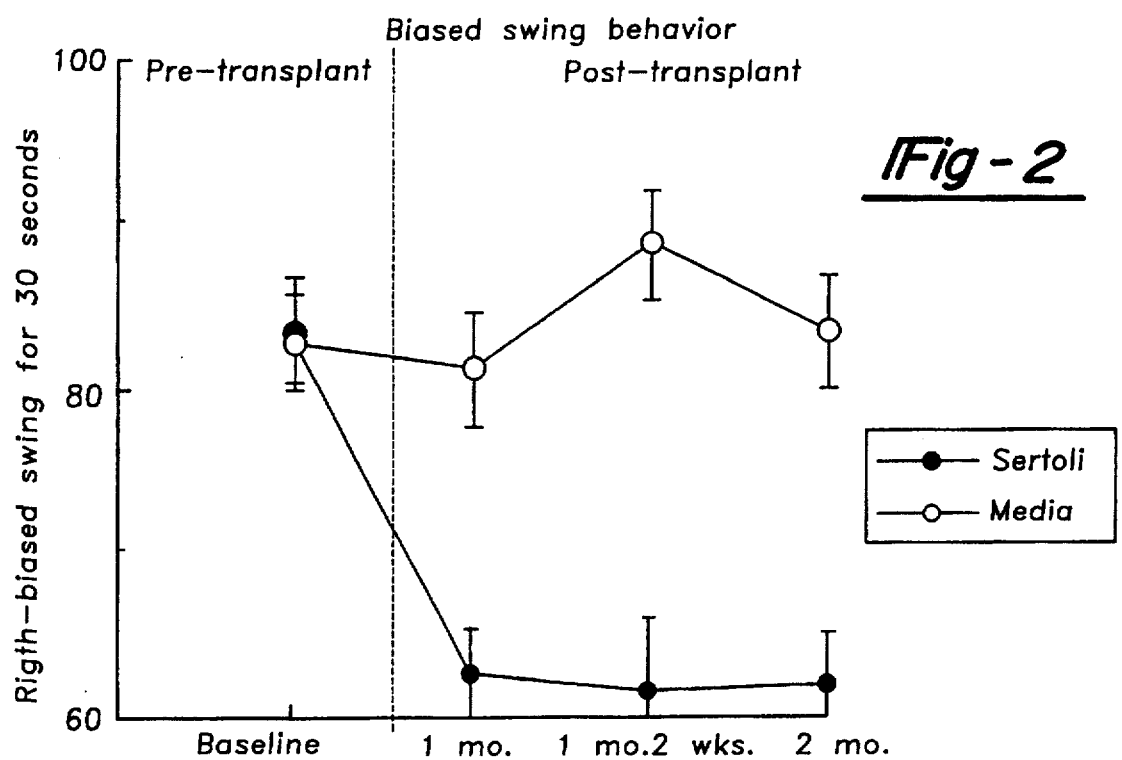
FIG. 2 is a graph showing biased swing behavior. Animals from both groups displayed >80% biased swing activity (contralateral to the lesion) as revealed by the elevated body swing test. At post-transplant periods, animals receiving the media alone continued to display significant biased swing activity. In contrast, animals receiving the Sertoli cells did not exhibit any biased swing behavior across the post-transplant periods.

The animals receiving Sertoli cells exhibited significant reductions in rotations (mean of 50 turns for 30 minutes) while the animals receiving the media above were at pre-transplant rotational level (FIG. 1). The normalization of turning behavior persisted across the two month test period. The right-biased swing activity previously displayed by the Sertoli cells transplanted animals was also significantly reduced at post-transplant test sessions (FIG. 2). The animals receiving the media did not show any significant reductions in their right-biased swing responses.

At autopsy, brains were removed from the animals and fixed for vibratome sectioning at 40–80 µm. Following staining, there was a marked reduction of activated glial cells at the penetration site (i.e., lesion site) in Sertoli cell transplanted rats when compared to the penetration site in the lesioned animals not transplanted with Sertoli cells.

These results, taken together, show that the Sertoli cells ameliorate the behavioral deficits of this animal models of Parkinson's disease. The mechanism involved is most likely the secretion of Sertoli cell-derived growth and regulatory factors which promote the repair and the prolonged support of the relevant nervous tissue. Additionally, Sertoli cells may promote nervous tissue repair in the brain by inhibiting glial cell activation at the lesion site.

Throughout this application various publications are referenced by citation or number. Full citations for the publication are listed below. The disclosure of these publications in their entireties are hereby incorporated by reference into this application in order to more fully describe the state of the art to which this invention pertains.

The invention has been described in an illustrative manner, and it is to be understood the terminology used is intended to be in the nature of description rather than of limitation.

Obviously, many modifications and variations of the present invention are possible in light of the above teachings. Therefore, it is to be understood that within the scope of the appended claims, reference numerals are merely for convenience and are not to be in any way limiting, the invention may be practiced otherwise than as specifically described.

TABLE 1

I. Sertoli Cell-Derived Growth and Regulatory Factors (Partial List)

| Category and Protein | Function |
| --- | --- |
| Hormones/Growth Factors | |
| Mullerian Inhibiting Substance | inhibits Mullerian duct |
| Inhibin | inhibits FSH release |
| Insulin-like Growth Factor (Sommatomedins A and C, IGF) | growth factor |
| Prodynorph in | |
| Interleukin-1α | mitogen |
| Transforming Growth Factor α & β | growth factors |
| Basic Fibroblast Growth Factor | growth factor |
| LHRH-like Factor | Leydig cell steroidogenesis |
| (unpurified or incompletely characterized) | |
| Sertoli Secreted Growth Factor | growth factor |
| Seminiferous Growth Factor | |
| Leydig Cell Stimulatory Activity | |
| Testins | |
| CMB proteins | |
| Vitamin Binding Proteins | vitamin transport |
| Transport and Bioprotection | |
| Transferrin | iron transport |
| Ceruloplasm | copper transport |
| Saposin | binds glycosphingolipids |
| SGP-2 (Clusterin) | lipid transport? |
| Androgen Binding Protein | transports T and DHT |
| SPARC | calcium binding protein? |
| IGF Binding Proteins | IGF transport |
| Riboflavin Binding Protein | riboflavin transport |
| Proteases and Protease Inhibitors | |
| Plasminogen Activator | protease |
| Cyclic Protein-2 | protease inhibitor |
| Cystatin | protease inhibitor |
| α$_2$-Macroglobulin | protease inhibitor |
| Type IV Collagenase | protease |
| Metalloproteinases | protease |
| Basement membrane | |
| Collagen IV | |
| Laminin | |
| Proteoglycans | |

REFERENCE CITED

Bjorklund and Stenevi, "Intracerebral neural grafting: a historical perspective" in Bjorklund, A and U. Stenevi, eds. *Neural grafting in the mammalian CNS*, Amsterdam: Elsevier, 3–11 (1985).

Bjorklund, "Dopaminergic transplants in experimental Parkinsonism: Cellular mechanisms of graft-induced functional recovery" *Current Biology*, 2:683–689 (1992).

Cameron et al., "Successful islet/abdominal testis transplantation does not require Leydig cells" *Transplantation*, 50:649–653 (1990).

Cameron and Muffly, "Hormonal regulation of spermatid binding to Sertoli cells in vitro." *J. Cell Sci.*, 100:523–533 (1991).

Griswold, "Protein Secretion by Sertoli cells: general considerations" in Russell, L.d. and M.D. Griswold eds. The Sertoli Cell, Cache River Press, Clearwater, Fla., 195–200 (1992).

Isacson et al., "Graft-induced behavioral recovery in an animal model of Huntington's disease" *Proc. Natl. Acad. Sci.*, 83:2728–2732 (1986).

Lindvall et al., "Transplantation in Parkinson's disease: two cases of adrenal medullary grafts to the putamen" *Ann. Neurol.* 22:457–468 (1987).

Lindvall et al., "Grafts of fetal dopamine neurons survive and improve motor function in Parkinson's disease" *Science*, 247:574–577 (1990).

Pakzaban et al., "Increased proportion of Ache-rich zones and improved morphological integration in host striatum of fetal grafts derived from the lateral but not the medial ganglionic eminence" *Exp. Brain Res.*, 97:13–22 (1993).

Sanberg et al., "Cell transplantation for Huntington's disease" R.G. Landes Co., Boca Raton, Fla, pp.19–21 (1994).

Selawry and Cameron, "Sertoli cell-enriched fractions in successful islet cell transplantation" *Cell Transplan.*, 2:123–129 (1993).

Wictorin et al., "Reformation of long axon pathways in adult rat CNS by human forebrain neuroblasts" *Nature*, 347:556–558 (1990).

What is claimed is:

1. A method of generating in situ trophic factors for ameliorating behavioral deficits caused by Parkinson's Disease by transplanting sertoli cells utilizing stereotaxic delivery into the brain of an adult a mammal who suffers from Parkinson's Disease, ", wherein said Sertoli cells express trophic factors comprising growth factors and immunosuppressive factors."

* * * * *